United States Patent [19]
Harris et al.

[11] Patent Number: 5,468,605
[45] Date of Patent: Nov. 21, 1995

[54] TRANSVERSE FLOW PLUNGERS FOR MICROPHYSIOMETERS

[75] Inventors: Albert K. M. Harris, Livermore, Calif.; Gregory L. Kirk, Montgomery Township, Somerset County, N.J.; John C. Owicki, Palo Alto, Calif.; Timothy D. Dawes, Scotts Valley, Calif.; Richard C. Kuo, Fremont, Calif.

[73] Assignee: Molecular Devices Corp., Sunnyvale, Calif.

[21] Appl. No.: 137,605

[22] Filed: Oct. 15, 1993

[51] Int. Cl.$^6$ ............ C12M 1/34; C12M 1/40; C12Q 1/02; C12Q 1/25
[52] U.S. Cl. ............ 435/4; 204/403; 435/29; 435/817; 435/284.1; 435/286.5; 435/287.1; 435/287.2
[58] Field of Search ............ 435/285, 817, 435/288, 4, 299, 310, 29, 291; 204/403

[56] References Cited

U.S. PATENT DOCUMENTS

| | | | |
|---|---|---|---|
| 5,104,804 | 4/1992 | Humphries et al. | 435/291 |
| 5,206,170 | 4/1993 | Sato et al. | 435/288 |
| 5,250,419 | 10/1993 | Bernard et al. | 435/288 |
| 5,312,762 | 5/1994 | Guiseppi-Elie | 436/806 |
| 5,395,503 | 3/1995 | Parce et al. | 204/403 |

OTHER PUBLICATIONS

Science, vol. 246, issued 13 Oct. 1989, Parce et al., "Detection of Cell-Affecting Agents with a Silicon Biosensor", pp. 243–247.

*Primary Examiner*—Jeffrey E. Russel
*Attorney, Agent, or Firm*—Banner & Allegretti, Ltd.

[57] ABSTRACT

One aspect of the invention is the method of operating a microphysiometer including a plunger assembly having a plunger body with a microchamber at one end for receiving a sample and a passage in the plunger body communicating with the microchamber comprises passing a medium transversely through the sample in the microchamber. Another aspect of the invention is the construction of the plunger assembly wherein the sample is positioned in the microchamber and the passage and microchamber are constructed and arranged so that medium flow is transverse through the sample. The sample may be a tissue slice retained between a pair of screens or membranes, adherent cells on a mesh screen or non-adherent cells retained in a chamber defined by a washer and a pair of screens or membranes.

18 Claims, 7 Drawing Sheets

TRANSVERSE FLOW PLUNGERS FOR MICROPHYSIOMETERS

BACKGROUND OF THE INVENTION

This invention pertains to microphysiometers, and more particularly to improved flow plungers for microphysiometers.

In a known microphysiometer, exemplified for example in Humphries et al. U.S. Pat. No. 5,104,804, rigid inner and outer sleeves covered at one end with a porous membrane, together with spacing means, are fitted together such that when the inner sleeve is fully inserted into the outer sleeve, the membranes are separated by a spacing means. The spacing means and the inner and outer membrane form a microchamber having living cells trapped within. The sleeves are adapted to hold the microchamber containing the cells adjacent to a silicon electrode that forms one wall of a flat microchamber. Cells are retained within the internal cavity of the porous microchamber while liquid is permitted to flow essentially, above, between and below the membranes and around the cells. The principal direction of flow of the liquid is parallel to the plane of the membranes and the surface of the silicon electrode. Changes in the media surrounding the cells, such as pH changes, can be measured by the silicon electrode.

The microphysiometer of Humphries et al. U.S. Pat. No. 5,104,804 has been commercialized in the CYTOSENSOR microphysiometer, that is made by Molecular Devices Corporation, Menlo Park, Calif. CYTOSENSOR is a registered trademark of Molecular Devices Corporation.

In the present plunger in the CYTOSENSOR device, the fluid flows tangentially across the upper surface of the cell-containing region, and the cells are in between the sensor and the flowing fluid. A consequence of this arrangement is that when fluid flow resumes during operation of the instrument, fresh medium must pass through the layer of cells before it gets to the surface of the sensor. If the cells are in a clot, then the surface of the sensor is accessible only by diffusion and not by bulk flow. The fluid exchange borders on the marginal for non-adherent cells and tangential flow is completely inadequate for thicker, contiguous samples such as tissue slices (typically 200–400 μm rather than 50 μm).

An object of the present invention sample is to provide an improved microphysiometer including a unique flow plunger and microchamber wherein the flow of medium is between the sample and a sensor and is then transverse and through the sample or around the sample, instead of tangential or across the sample.

Another object of the present invention is to provide an improved microphysiometer wherein fresh medium, from a passage means, flows directly between the cells and one wall of the microchamber, and where the wall is spaced from 10 microns to 200 microns from the sample for improving both the culture conditions (e.g., oxygenation) and the time response of the micro physiometer.

Yet another object of the present invention is to provide an improved microphysiometer wherein the time resolution of the acidification rate measurement is improved by increasing the rate of pH recovery when flow turns on. Further, time resolution for the physiological measurement is maintained by maintaining rapid diffusive communication between sample and sensor. Other objects and advantages will become more apparent hereinafter.

SUMMARY OF THE INVENTION

This invention pertains to a method of operating a microphysiometer including a plunger assembly having a plunger body with a microchamber at one end for receiving a sample that maintains diffusive contact between the sample and a wall of the microchamber and passage means in the plunger body communicating with the microchamber comprising the steps of passing a medium through the passage means and directing the medium between the wall and the sample in the microchamber. Preferably, said wall of the microchamber comprises a sensor. Further, the method comprises maintaining as small a distance as possible between the sample and sensor in order to maximize the results. Preferably, the space between the sample and the sensor is on the order of 10–200 μM.

Another aspect of this invention lies in the plunger assembly having a plunger body with inlet and outlet passages communicating with a microchamber at one end of the plunger body, with the microchamber and inlet and outlet passages constructed and arranged so that flow of medium is between the sample and a wall of the microchamber defined by a sensor and then between the sample and a wall of the microchamber and then transverse through or around the sample in the microchamber.

BRIEF DESCRIPTION OF THE DRAWING

There is shown in the attached drawing presently preferred embodiments of the present invention wherein like numerals refer to like elements in the various views and wherein.

DETAILED DESCRIPTION OF THE PRESENT INVENTION

Figure 1:
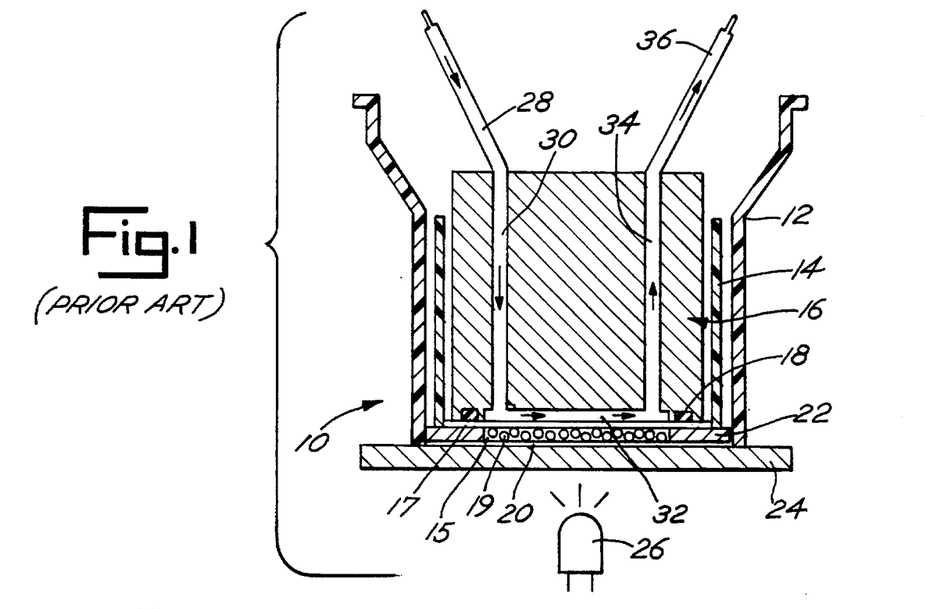
FIG. 1 is a schematic cross-sectional view of a prior microphysiometer cell capsule and plunger.

There is shown in FIG. 1 a prior art device 10 which includes a membrane cup or sleeve 12 that is open at the upper end. Disposed within the membrane cup 12 is a membrane insert 14 that is also open at its upper end for receiving a plunger 16. The plunger 16 is engaged at its bottom by a plunger O-ring 18 for sealing the bottom of the plunger 16 against porous membrane 17. A microchamber 15 for receiving cells 19 is defined between porous membrane 17, porous membrane 20 and annular spacer 22. The microchamber 15 is relatively flat, i.e., it has a large ratio of width or diameter to height and has a volume between 10 nanoliters and 10 microliters. Silicon electrode 24 is adjacent to and parallel to the outer surface of membrane 20 so that changes in the solution caused by the cells, such as pH, can be detected by the silicon electrode or sensor 24. An LED 26 is provided adjacent sensor 24, which may be of the type described in U.S. Pat. Nos. 4,519,890, 4,704,353 and 4,741,619. Solution is conducted from the fluid inlet 28, through passages 30, 32, and 34 in the plunger 16 and exits from fluid outlet 36.

It is seen from the arrows in passage 32, that fluid flows tangentially across membrane 17, which defines the upper surface of the cell-containing region or microchamber 15 and that the cells 19 are in between the sensor 24 and the fluid flowing in passage 32. As a consequence of this arrangement, fresh medium must pass through the layer of cells before it gets to the surface of the sensor. If the cells are in a clot, the surface of the sensor 24 is accessible only to diffusion and not to bulk flow.

For any microphysiometer, the distance between the surface of the biological sample and the face of the sensor is a crucial parameter, which strongly influences the time response and sensitivity of the device. These statements follow from the fact that transport of protons and other dissolved materials within the volume between the sample and sensor is diffusive during the periods when flow is off.

To be more quantitative, call the distance between sample and sensor r and the diffusion coefficient of a solute D. Then elementary considerations of diffusion dictate that the characteristic time $\tau$ for diffusive transport across the distance r is about $r^2/(2D)$. This can be interpreted as a "dead time" for transport from the sample to the sensor or as a time constant for spatial equilibration in the volume for solutes produced or consumed by the cells. Note that $\tau$ is proportional to $r^2$, so that the temporal resolution of measurements degrades rapidly with increasing distance between sample and sensor. For example, if $D\sim 10^{-5} cm^2/s$ and $r=100$ μm$=0.01$cm, then the value of $\tau\sim 5s$. But if $r=1000$ μm$= 0.1$ cm, then the value of $\tau\sim 500s$.

Another reason to make r (and, hence the volume) small is to increase the sensitivity of measurements. For a given number of protons excreted by the cells, the extracellular pH change is inversely proportional to the extracellular aqueous volume. System sensitivity is limited by the minimum measurable pH change. Similar considerations hold for measurement of other solutes excreted or consumed by the cells.

The essence of the new plunger design is to cause the flow of medium to be transverse, through and/or around the sample instead of across its top, while maintaining as small a distance as possible between the sample and the sensor.

FIGS. 2–6 show a first embodiment of the new plunger. Plunger 116 comprises a generally cylindrical body having an inlet tube 128 affixed in an opening 129 in the plunger 116. The tube 128 defines a passage 130 therein. An outlet tube 136 is affixed in an opening 137 in the plunger and the tube 136 a passage 134 therein. The plunger 116 bears upon the top of the silicon electrode or sensor 124 and is in sealing relationship thereto through O-ring 118 which is disposed in a recess 121 in the body of plunger 116.

Figure 2:
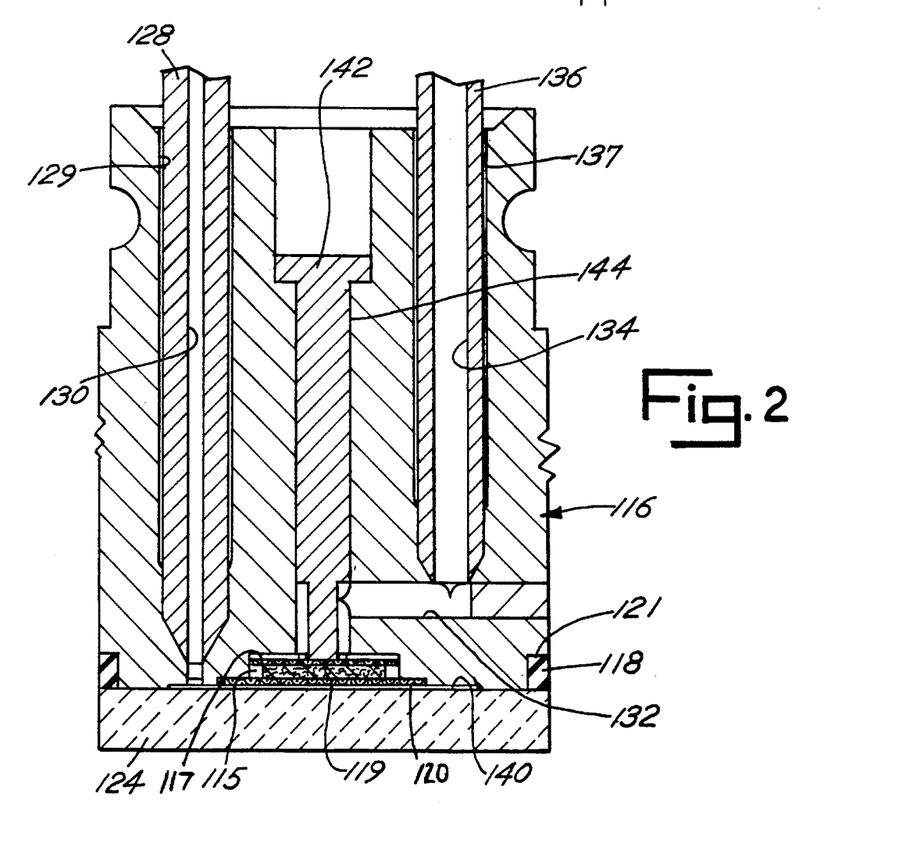
FIG. 2 is a cross-sectional view, similar to FIG. 1, of the present invention.
Figure 3:
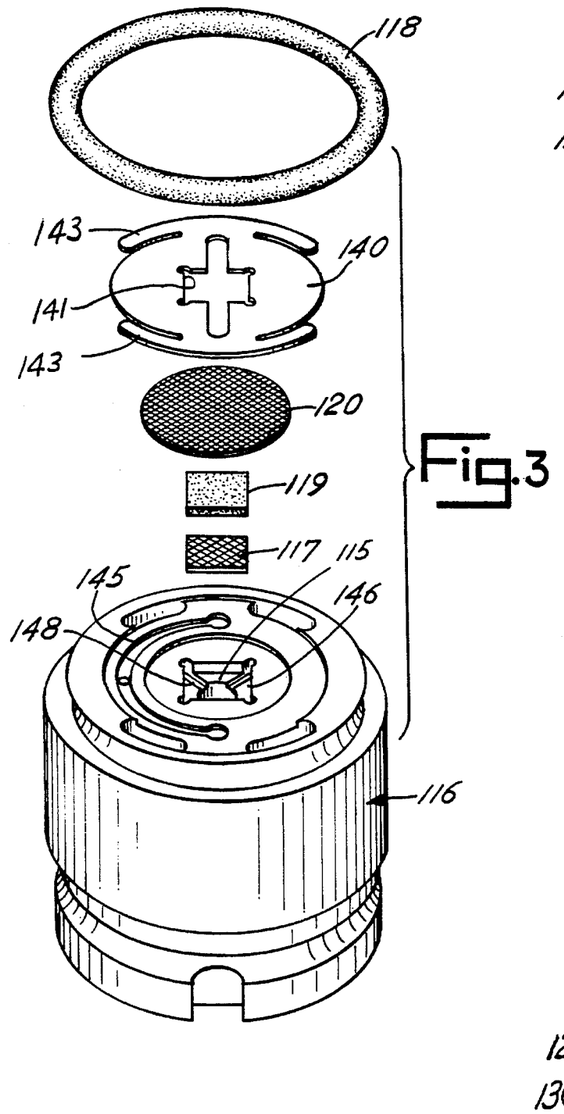
FIG. 3 is an exploded view of the plunger of the present invention, in an inverted position as compared with FIG. 2.
Figure 4:
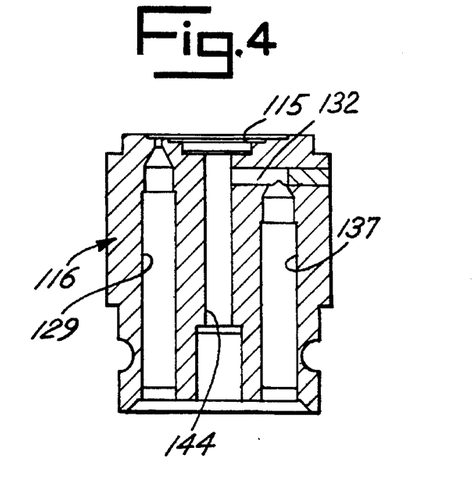
FIG. 4 is a cross-sectional view of the plunger of FIG. 3.
Figure 5:
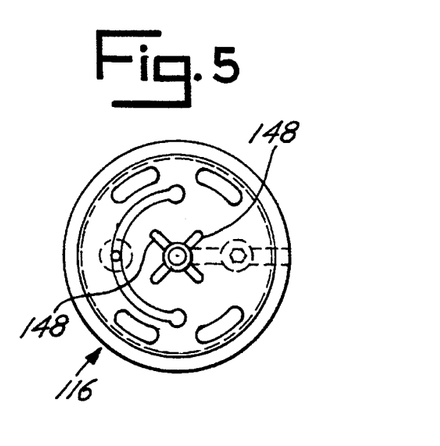
FIG. 5 is a bottom view of the plunger of FIG. 4.
Figure 6:
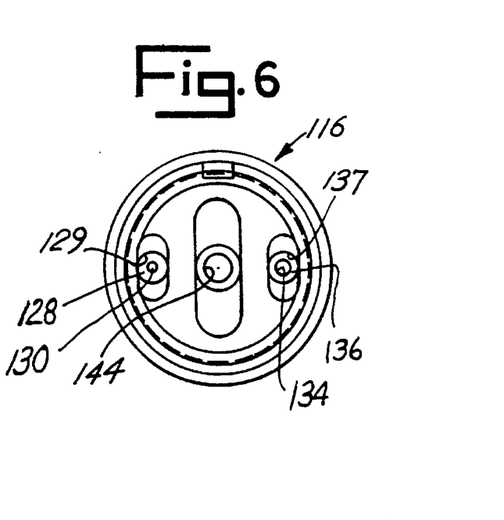
FIG. 6 is a top view of the plunger of FIG. 4.

As shown in FIGS. 3 and 4, there is defined within the plunger 116 a microchamber 115 that has a small height to width or area ratio for receiving tissue or cells 119. The tissue 119 is retained between screens or porous membranes 117 and 120. The tissue sample is spaced away from the sensor by the thickness of the screen 120 and the spacer 140. Presently, the sample-sensor spacing is approximately 150 μm (100 μm thick screen plus 50 μm thick spacers). Acceptable time response can be achieved with spacing up to approximately 200 μm. Time response improves with decreased spacing down to the practical limit of about 10 μm imposed by the constraints of fluid engineering. The tissue slice, about 2 mm square and typically 300 μm thick, is sandwiched between the porous membranes 117 and 120, which are preferably made from woven mesh. The tissue slice may be between 100 and 400 μm thick. Woven mesh has been found to be less resistant to flow than the polycarbonate membranes used in prior cell capsules because of its greater open area. A spacer 140 is provided between the porous membrane 120 and the silicon electrode or sensor 124 (FIG. 2), which comprises one wall defining the microchamber 115. The spacer 140 is relatively thin so as to space the sample on the order of 10–200 μm from the silicon electrode 124. The spacer 140 has a central opening 141 and a plurality of tabs 143 for securing the spacer to the plunger 116. A contact pin 142 (FIG. 2) is provided in a central opening 144 in plunger 116 to couple the electrical signal through the conducting solution from the central sensing spot on the silicon electrode 124. The contact pin 142 also provides top support for the sample to allow fluid to escape through to the exit passages 132 and 134 (FIG. 2).

The plunger 116 and spacer 140 work together to channel the fluid from inlet tube 128, around the semi-circular groove 145 in the plunger 116, through the spacer 140, along the top of the chip or sensor 124, and through or around the tissue 119 sandwiched between the two membranes or screens 117 and 120, past the contact pin 142, and to exit through passages 132 and 134 in the plunger 116. The contact pin 142 and the recess channels 148 serve to create a path for the fluid to escape past the sample towards the exit passages 132 and 134.

The user interface for the plunger of the present invention is quite different from that for prior microphysiometers. In prior known devices, the cells are loaded into a cell capsule, which is transferred to the microphysiometer. The plunger is inserted as a final step to form the flow chamber (e.g., FIG. 1). However, in the present invention, the sample, e.g., the tissue slices 119 are loaded into an upside-down plunger 116 (FIG. 3) with fluid priming. The porous membranes 117 and 120 are disposed above and below the tissue slices 119 and the spacer 140 is positioned over the screen 120 and secured to the plunger 116. The plunger 116 is mounted in a flow chamber with the silicon electrode 124 in its base. The chamber assembly is then installed in the microphysiometer. In practicing the present invention, the tissue slice 119 is sandwiched between a pair of screens or porous members and then the sandwiched tissue slice is placed in the microchamber prior to joining medium transversely therethrough.

Figure 7:
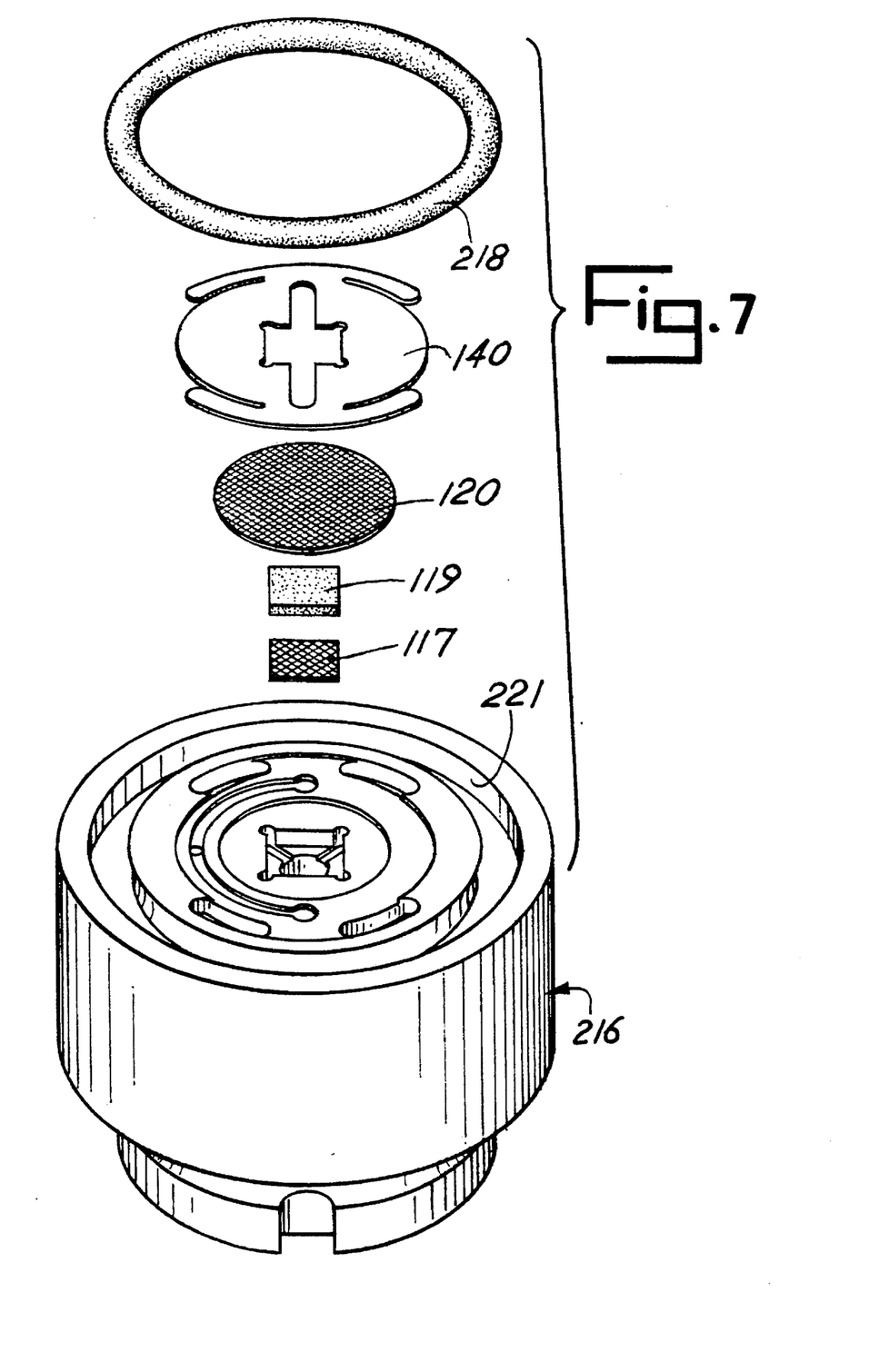
FIG. 7 is an exploded view of a modified plunger in a inverted position as compared to FIG. 2, wherein an O-ring is placed in an annular recess in the plunger rather than a circumferential recess on the plunger.

The plunger embodiment of FIG. 7 is like that of FIG. 3 except that the O-ring 218 is retained in a groove or recess 221 in the plunger body 216, rather than an external groove. Otherwise, the plunger of FIG. 7 functions the same as the plunger of FIG. 3.

Brain tissue slices are quite sensitive to oxygen deprivation and it has been found desirable to increase the oxygen concentration of the medium in the chamber 115 by flooding the atmosphere in the debubbler of the microphysiometer with pure oxygen.

Beyond tissue slices, there are other applications for which known tangential-flow plungers are poorly suited. These other applications include adherent cells and pH-changing enzymes. For example, with muscarinic responses of TE 671 cells, the time resolution that can be obtained from the prior art device is inadequate to capture the quick and complicated kinetics of the response of these cells due to poor fluid exchange. The problem is compounded by the rapid growth habit of the cells. Unless the cells are handled with great precision, they overgrow the surface of the capsule cup or membrane cup, plugging the pores of the membrane and severely limiting fluid exchange.

Another example where a tangential-flow plunger is inadequate involves pH-changing enzymes in the microphysiometer. If an acidifying enzyme, such as acetylcholinesterase, is attached to a solid support such as a nitrocellulose membrane and put inside a known cell capsule (as in FIG. 1) in lieu of cells, fluid exchange is poor.

Figures 8, 9:
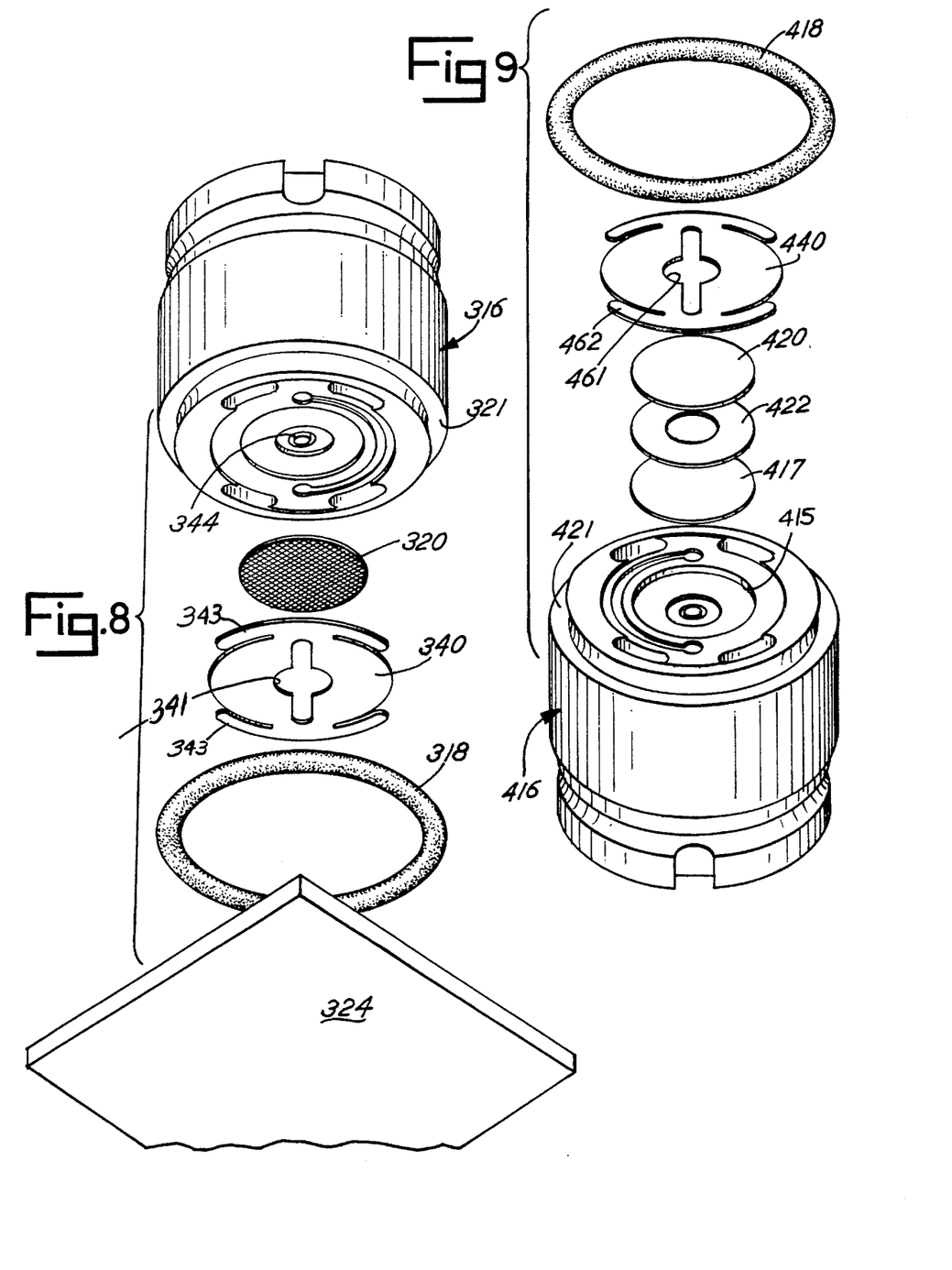
FIG. 8 is an exploded view of another modification of the plunger.
FIG. 9 is an exploded view of yet another modification of the plunger in an inverted position as compared to FIG. 2.

A transverse-flow plunger as shown in FIGS. 8 and 9 would be suitable for adherent cells growing on a porous mesh or a membrane containing immobilized enzymes. The plunger 316 is similar to plunger 116, except that the center opening is differently configured. Instead of the generally square countersunk form 146 with recesses 148 for receiving screen 117 and tissue 119, as in FIGS. 3 and 4, for example, there is a central circular opening 344. The adherent cells are grown on membrane or meshscreen 320 or enzymes are trapped on membrane 320. FIG. 8 illustrates the assembly of the plunger and FIG. 9 illustrates the parts inverted in the use condition, but with the parts in exploded view. Also, sensor 324 is illustrated in FIG. 8. The plunger 316 includes an annular recess 321 for receiving the O-ring 118. The spacer 340 has a central opening 341 and a plurality of tabs 343 for securing the spacer to the plunger 316. The plunger 316 is designed to force fluid transversely through the sample on the membrane or screen 320. Bypassing flow around the edges, as in the case of tissue slices, is not allowed in this application.

Figure 10A:
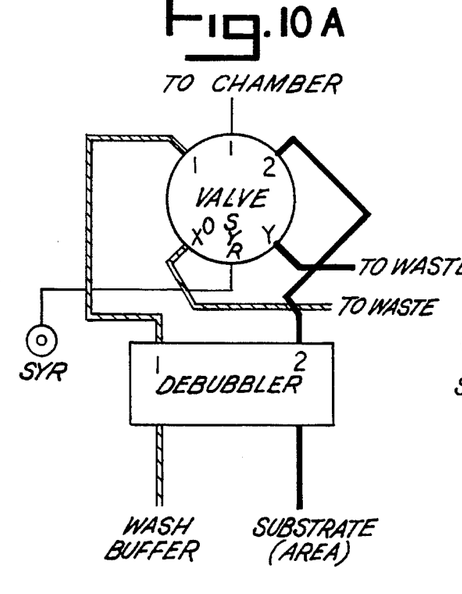
FIG. 10A is a fluidic configuration for delivering enzyme substrate.
Figure 10B:
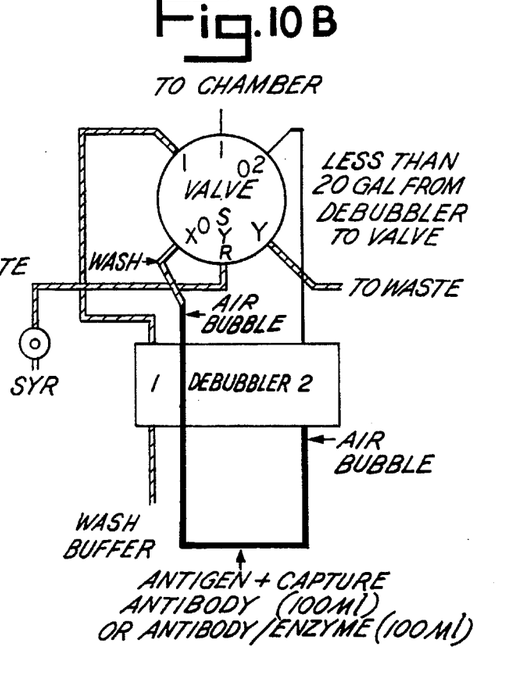
FIG. 10B is a fluidic configuration for delivering antigen and capture antibody.
Figure 11:
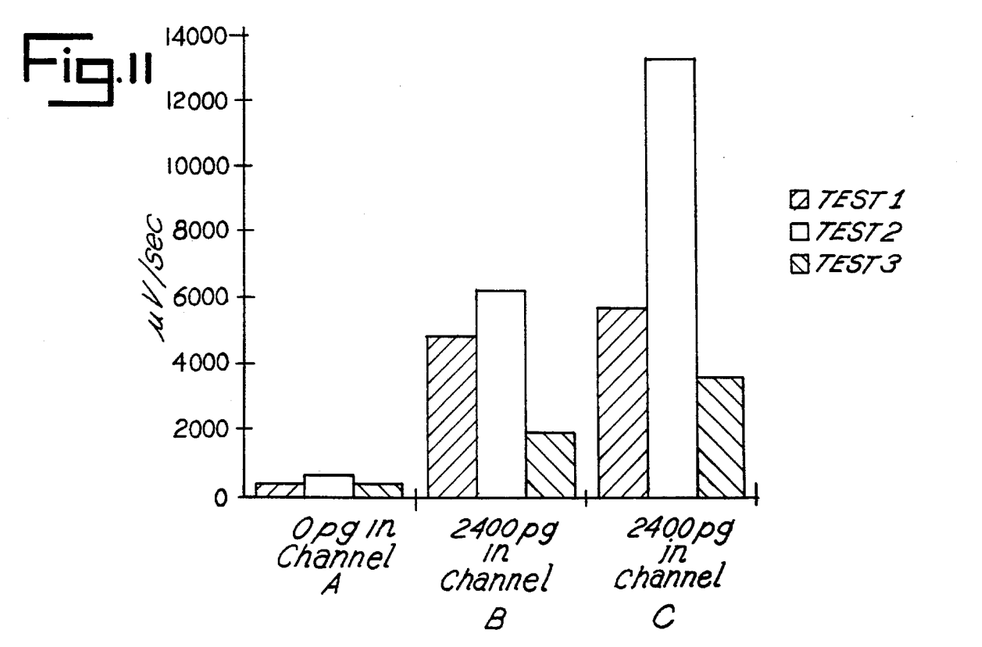
FIG. 11 shows the results of an immunoassay.
Figure 12:
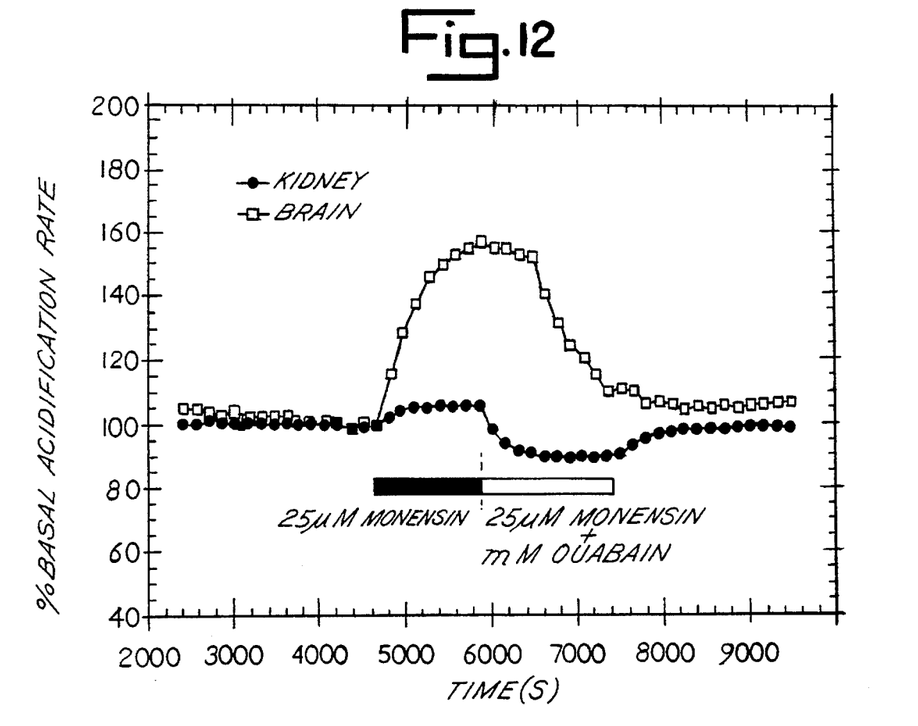
FIG. 12 is a plot of acidification rate versus time for a kidney slice.

In one experiment, the plunger 316 of FIG. 8 was used to perform immunoassays using the Cytosensor™ Microphysiometer described previously. As seen in FIG. 8, the filtration membrane is located precisely where the screen holding the tissue slice would be. The fluid containing the sample (ricin toxin A chain) is preincubated with capture reagent (biotinylated antibody & fluoresceinated antibody) and loaded into the Cytosensor device through the injection loop (roughly 200 μl). The sample/capture reagent bolus is then filtered through the membrane in the plunger using the regulated peristaltic pumps of the Cytosensor device. This is followed by a bolus of Enzyme Reagent (anti-fluorescein-urease, 100–400 μl). FIG. 10B shows the configuration of fluid lines on Cytosensor necessary to deliver the sample/capture reagent and enzyme reagent to the membrane. Air bubbles are used to keep the fluid boluses intact. They are removed by the debubbler just before delivery to the plunger. After complete antibody/sample antibody/enzyme complexes have been formed on the membrane, the substrate is delivered to the plunger using the fluidics as set up in FIG. 10A. When the substrate flow stops the alkaline product of the enzyme reaction builds up in the microchamber defined in the transverse flow plunger. The rate of pH increase is a direct measure of enzyme, hence ricin, content on the membrane with a small contribution due to background non-specific enzyme binding. FIG. 11 shows the results of three trials with two plungers. The results demonstrate the ability to readily discriminate between 2.4 ng ricin samples and blank test samples.

An improvement to all the transverse plunge designs shown in FIGS. 2–9 involves improving the stated object of the invention to decrease pH recovery time through improved fluid washout. This is accomplished by minimizing the volume of fluid that is communicating with the sensing region, inlet and outlet passages, but that is not directly in the flow path. In particular, the diameter of the screen or membrane disk 120 can be reduced to a diameter just larger than the square countersink or recess 146, or the circular opening 344.

FIG. 9 shows a further modification of plunger 416 wherein non-adherent cells are retained in a hold chamber defined between the membranes 417 and 420 and the washer 422. The spacer 440 having a central body with an opening 461 therethrough and four tabs 462 extending therefrom is adapted to secure the membranes 417, 420 and washer 422 in place in microchamber 415 on the end of the plunger 416. Non-adherent cells may be added with an immobilizing matrix to secure them between the membranes 417 and 420 with more stability. The O-ring 418 is adapted to be received in annular recess 421 in the plunger 416.

Typically, flow rates are 15–100 μl/minute and sample size is 2 mm by 2 mm square and from 100 μm–400 μm thick. The rate of pH change is from 10 to 1000 milli pH units/minute.

Alternatively, non-adherent cells can be immobilized in a matrix, say a fibrin gel clot, which is then transferred by spatula or pipette into the recess 146 in first embodiment of the transverse flow plunger showing FIGS. 2–6. Screens 117 and 120 are used to retain the cell-matrix.

Biological applications of the transverse flow plungers include tissue slices nonadherent cells, and adherent cells grown on mesh.

I. Results for Tissue Slice Experiments

Kidneys were excised from male Sprague-Dawley rats and split lengthwise into halves with a razor blade. The halved sections were then cut into 300 μm thick slices with a McIlwain model tissue chopper. The kidney slices were placed in a petri dish containing DMEM medium and further trimmed with surgical scissors to fit within the 2 mm by 2 mm square recess of the plunger. With the plunger inverted, the rubber O-ring was inserted in its groove and the square top mesh screen placed in the recess of the plunger. The kidney slice was laid in the recess on top of the square top mesh screen, the bottom round screen placed over the kidney slice, and the spacer locked in place by its tabs using fine forceps. The entire plunger arrangement of FIG. 2 was then inverted into a microphysiometer sensor chamber and loaded onto the microphysiometer, for example, a CYTOSENSOR microphysiometer made by Molecular Devices Corporation, Menlo Park, Calif. The procedure for loading tissue slices and maintaining viability of the slices (as measured via acidification rates) has been repeated with rat brain, heart, adrenal gland and spleen in addition to kidneys and liver. DMEM medium without bicarbonate was continuously flowed through the system at approximately 100 μl/min for the duration of the experiment. After monitoring acidification rates for 25 hours, 25 μM monensin and then 25 μM monensin plus 100 mm ouabain was applied to kidney and brain slices with the results as shown in FIG. 12. Monensin, a sodium-proton exchanger, increases acidification rates by increasing both sodium coupled proton afflux from the cells of the kidney slice and ATP hydrolysis by the Na+/K+ATPase. Ouabain acts primarily by inhibiting the Na+/K+ATPase. This inhibition decreases both ATP hydrolysis and sodium coupled proton afflux from the cells through a decrease in the sodium gradient caused by monensin. The effects of these mechanisms are a decrease in acidification rates below the initial baseline acidification rate as seen in FIG. 12.

Figure 13:
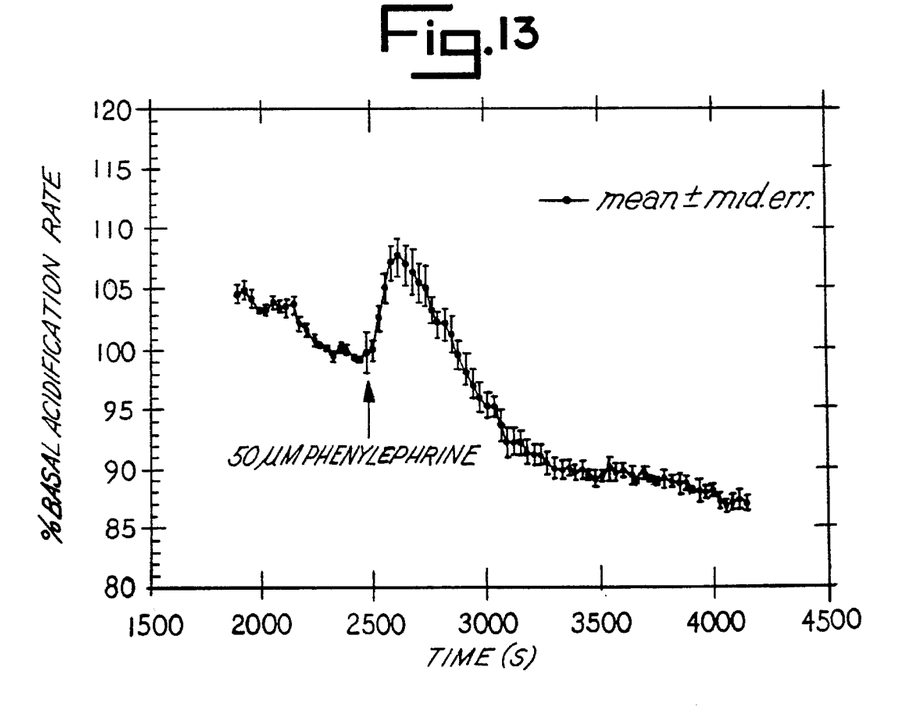
FIG. 13 is a plot of acidification rate versus time for a liver slice.

In FIG. 13, pharmacological responses of liver slices to 50 μM phenylephrine are shown. As with kidneys, livers were excised from male Sprague-Dawley rats. Sections of liver were then cut into 200 μM slices using a McIlwain tissue chopper and loaded into transverse flow plungers as noted above. MEM medium without bicarbonate continuously perfused the liver slices within the plunger throughout the experiment. Slices were exposed to 50 μM phenylephrine for 30 s, with the acidification rate response shown in FIG. 13. Phenylephrine, an $a_1$-adrenergic agonist, is known to act through an $IP_3$ pathway that increases intracellular calcium and activates PKC. Physiologically, phenylephrine activates glycogenolysis and gluconeogenesis.

II. Non-Adherent Cells

Figure 14:
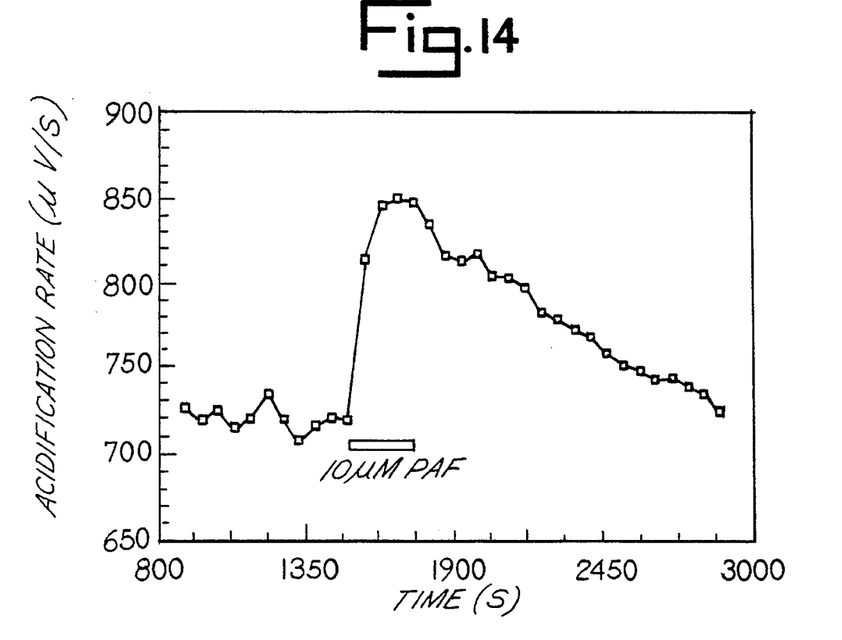
FIG. 14 is a plot of acidification rate versus time for TF-1 non-adherent cells.
Figure 15:
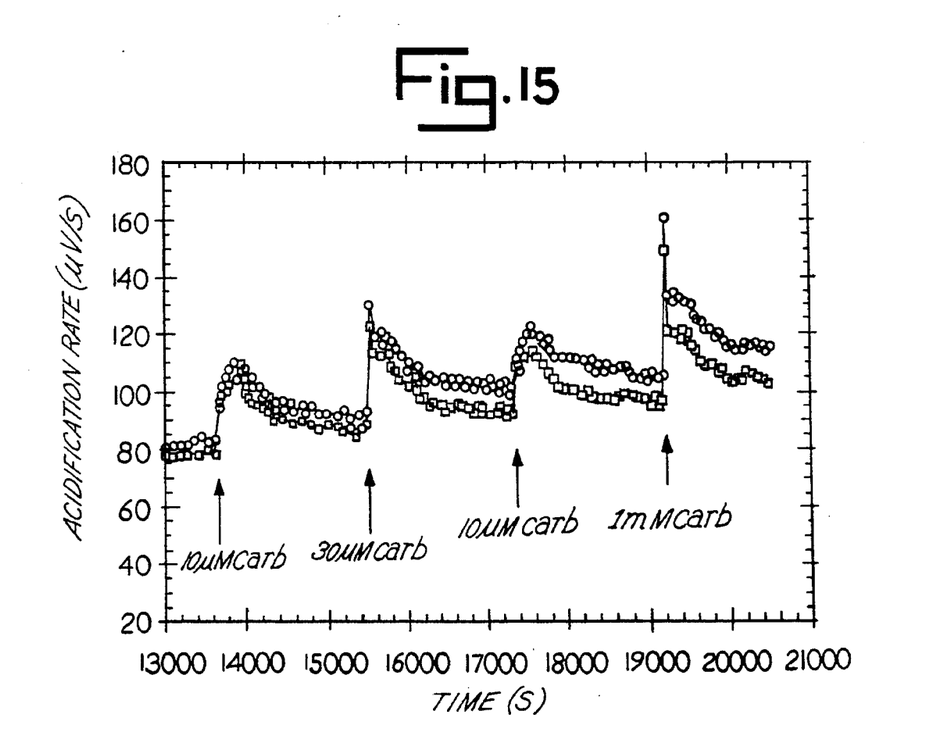
FIG. 15 is a plot of acidification rate versus time for M1WT3 adherent cells.

It is also possible to immobilize non-adherent cells within a fibrin matrix in the square well of the plunger shown in FIG. 3. Cells are first centrifuged at 500 g for 5 min and resuspended at the desired concentration in a fibrinogen entrapment reagent available through Molecular Devices Corporation (Menlo Park, Calif.). 200 μl of cells and fibrinogen entrapment reagent were then mixed with 200 μl of thrombin entrapment reagent, also from Molecular Devices Corporation. 400 μl of this mixture was then pippetted onto a square top mesh screen (used with tissue slice plungers of FIG. 3) lying in a well of a 96 well microtiter plate. After allowing 10 min for the fibrin clot to form, the entire clot was lifted from the well by pinching a corner of the square mesh and laid in an inverted plunger with the square mesh forming a bottom support for the fibrin clot. The O-ring was inserted in its groove, the bottom round mesh screen placed over the fibrin clot, and the spacer locked into place by its tabs with fine forceps. The entire plunger arrangement was then inverted into a standard CYTOSENSOR microphysiometer sensor chamber and loaded on the CYTOSENSOR microphysiometer. FIG. 14 shows acidification rate data collected for TF-1 cells exposed to 10 μM platelet activating factor (PAF) for 5 min. PAF activates the inositol triphosphate ($IP_3$) signal transduction pathway, causing an increase in intracellular $Ca^{+2}$ concentration and activation of protein kinase C (PKC). This has multiple cellular effects, but the increased acidification rates are primarily the result of activation of the Na+/H+ exchanger and increased cellular glycolytic activity. FIG. 15 shows pH vs. time data for the same TF-1 cells comparing acid clear out between a CYTOSENSOR capsule cup tangential flow system and the inventive transverse flow system of FIGS. 2–6. Clearly, the plunger of this invention has a much faster acid clear out time (2 seconds vs. 20 to 25 seconds for the CYTOSENSOR microphysiometer cell capsule).

III. Adherent Cells Grown on Mesh

Adherent M1WT3 cells were cultured for 9 days on 5 mm diameter, 80 μm pore size, plasma etched polyester mesh screens in 12 well tissue culture plates with Ham's F12 medium containing 10% fetal bovine serum (FBS). Prior to use on the CYTOSENSOR microphysiometer, WT3 cells were serum starved by moving the screens from wells containing Ham's F12 medium containing 10% FBS to wells containing only Ham's F12. Mesh screens were loaded into inverted plungers with the surface of the mesh screens facing the bottom of the 12 well tissue culture plate facing the surface of the LAPS chip. The O-ring was then inserted in its groove and the top spacer locked in place by its tabs. The entire plunger arrangement (FIG. 3) was then inverted into a CYTOSENSOR microphysiometer sensor chamber and loaded onto the microphysiometer. The M1WT3 cells are CHO-K1 cells transfected with the $M_1$ muscarinic receptor which is activatable by carbachol, an acetylcholine analog. The $M_l$ muscarinic receptor also signals through inositol triphosphate ($IP_3$) and causes an increase in acidification rates as seen in FIG. 15. This FIGURE shows a plot of M1WT3 cells to varying concentrations of carbachol.

There has been provided by the present invention novel plungers for a microphysiometer wherein flow of medium is transverse through or around the sample, whether the sample is a tissue slice, non-adherent cells or adherent cells grown on mesh, or the like.

We claim:

1. In a method of operating a microphysiometer including a plunger assembly having a plunger body with a microchamber at one end for receiving a sample that maintains diffusive contact between the sample and a wall of the microchamber, and inlet and outlet passage means in the plunger body communicating with the microchamber, the improvement comprising the steps of passing a medium through the inlet passage means and directing the medium on one side of the sample through the microchamber between the wall and the sample to the outlet passage means on the opposite side of the sample and, wherein the distance between the sample and wall is 10–200 μm.

2. The method according to claim 1 wherein the medium passed between the wall and the sample is further passed along the surface of and around the sample in the microchamber.

3. The method of claim 1 wherein said wall of the microchamber comprises a sensor.

4. The method of claim 1 including the step of sandwiching the sample between a pair of porous membranes.

5. The method of claim 1, wherein the sample is a tissue slice, and including the steps of sandwiching the tissue slice between a pair of screens and positioning the sandwiched tissued slice in the microchamber prior to passing medium therethrough on both sides of the tissue slice 6. The method of claim 5, wherein the tissue slice is between 100 and 400 μm thick.

7. The method of claim 4, wherein the sample is a collection of cells in an immobilizing matrix.

8. The method of claim 1 including the step of adhering the sample to a screen and positioning the screen and the sample in the microchamber for flow of medium along the surface of the sample.

9. A method according to claim 6, wherein the flow rate of the medium is 15 to 100 μl/minute.

10. The method of claim 1 including the steps of positioning a membrane containing immobilized enzymes in the microchamber.

11. For use in a microphysiometer, a plunger assembly comprising a plunger body having an inlet passage and an outlet passage therein for receiving and discharging a medium from the plunger body, a recess formed in an end of the plunger body and defining a microchamber for receiving a sample that maintains diffusive contact between such sample and a wall of the microchamber and that communicates with the inlet passage and the outlet passage, a sample, a means for retaining the sample in the microchamber, said inlet passage and said outlet passage each having openings to the microchamber, said openings being on opposite sides of the sample, said microchamber and inlet and outlet passages constructed and arranged so that flow of medium is first between the sample and said wall, and then on the opposite side of said sample, said microchamber having a spacing to place the sample between 10–200 µm from said wall.

12. A plunger assembly according to claim 11 wherein the outlet passage is arranged to flow the medium through the sample.

13. A plunger assembly as in claim 11 wherein the sample comprises a tissue slice and said means for retaining a sample including a first screen means and a second screen means on the side of the tissue, slice opposite the first screen means.

14. A plunger assembly as in claim 13 including spacer means for holding the first and second screen means and the tissue slice in said microchamber.

15. A plunger assembly as in claim 12 including a semi-circular groove in an end of the plunger body communicating the inlet passage and the outlet passage.

16. A plunger assembly as in claim 11 wherein said wall of the microchamber comprises a sensor.

17. A plunger assembly according to claim 11 wherein the medium passed between the wall and sample is further passed around the sample in the microchamber.

18. A plunger assembly according to claim 11 wherein the medium passed between the wall and the sample is further passed along the surface of and around the sample in the microchamber.

* * * * *